United States Patent [19]
Wong et al.

[11] Patent Number: 5,552,297
[45] Date of Patent: Sep. 3, 1996

[54] LEAD DETECTION METHOD AND REGGENTS UTILIZING AMINOLEVULINIC ACID DEHYDRATASE AND TERTIARY PHOSPHINES

[75] Inventors: Martin Wong, Grayslake; John M. Ramp, Gurnee, both of Ill.; John M. Brackett, Kenosha, Wis.

[73] Assignee: Abbott Laboratories, Abbott Park, Ill.

[21] Appl. No.: 419,845

[22] Filed: Apr. 11, 1995

Related U.S. Application Data

[63] Continuation of Ser. No. 171,035, Dec. 21, 1993, abandoned.

[51] Int. Cl.$^6$ .............................. C12Q 1/32; G01N 33/53
[52] U.S. Cl. .......................... 435/26; 435/7.71; 435/810; 436/74
[58] Field of Search ................................. 435/7.71, 7.91, 435/18, 26, 810; 436/63, 74, 172, 808, 815; 556/20, 21; 562/8; 568/8, 14; 987/121

[56] References Cited

U.S. PATENT DOCUMENTS

| | | | |
|---|---|---|---|
| 3,852,362 | 12/1974 | Lambert | 260/606.51 |
| 3,973,129 | 8/1976 | Blumberg | 250/461 B |
| 4,328,163 | 5/1982 | Hanssle | 260/439 R |

FOREIGN PATENT DOCUMENTS

WO9301310  1/1993  WIPO .

OTHER PUBLICATIONS

Wolff C., Metodo Simplificaso Para La Determin . . . Rev Med Chile 202:227–230 1974.

A. Berlin, et al., European Standardized Method for the Determination of δ–Aminolevulnic Acid Dehydratase Activity in Blood, *Z. Klin. Chem. Klin. Biochem.* S. 389–390 (1974).

P. N. B. Gibbs, et al., Purification and Properties of 5–aminolaevulinate dehydratase from human erythocytes, *Biochem. J.* 230, 25–34 (1985).

S. Sassa, Delta–Aminolevulinic Acid Dehydratase Assay, *Enzyme* 28, 133–145 (1982).

P. M. Anderson, et al., Purification and Properties of δ–Aminolevulinate Dehydrates from Human Erthrocytes, *The Journal Biological Chemistry*, vol. 254, No. 15, Issue of Aug. 10, 6924–6930 (1979).

M. T. Volosin, et al., Use of the Carbon Rod Atomizer for Analysis of Lead in Blood: Three Methods Compared, *Clinical Chemistry*, vol. 21, No. 13, 1986–1987.

J. O. Pierce, et al., Lead, Chromium, and Molybdenum by Atomic Absorption, *Arch Environ Health*, vol. 13, 208–212 (Aug. 1966).

D. R. Bevan, et al., Mechanism of Porphobilinogen Synthase, *The Journal of Biological Chemistry*, vol. 255, No. 5, Issue of Mar. 10, pp. 2030–2035 (1960).

P. M. Jordan, et al., Purification of Porphobilinogen Synthase from Bovine Liver, *Methods in Enzymology*, vol. 123, 427–434 (1986).

*Primary Examiner*—Ralph J. Gitomer
*Attorney, Agent, or Firm*—John F. Levis

[57] ABSTRACT

A method and kit for simplifying and improving the sensitivity and accuracy of a lead assay for a sample solution suspected of containing lead determines the extent of a reaction between a substrate and a disulfide enzyme in the presence of an activating reagent which contains a water-soluble tertiary phosphine reagent so as to increase the activity of the disulfide enzyme for reaction with the substrate. For a colorimetric determination of the enzyme activity a chromophore is formed upon reaction with a selected component of the sample solution in the presence of a colorimetric enhancing reagent. The colorimetric enhancing reagent contains a metal ion such as cupric ion or ferric ion which is soluble in the sample solution. The extent of the chromophore formation is then photometrically determined.

36 Claims, No Drawings

5,552,297

LEAD DETECTION METHOD AND REGGENTS UTILIZING AMINOLEVULINIC ACID DEHYDRATASE AND TERTIARY PHOSPHINES

This application is a Continuation of U.S. Ser. No. 08/171,035, filed Dec. 21, 1993, now abandoned.

FIELD OF THE INVENTION

The present invention relates to assays for detecting metal ions such as lead and, more particularly, utilizing selected reagents which simplify and improve the sensitivity and accuracy of a whole blood lead assay using a disulfide enzyme like aminolevulinic acid dehydratase.

BACKGROUND OF THE INVENTION

The rapid determination of trace metals in biological and environmental systems is increasingly important in identifying potential hazards and preserving the public health. The toxicity of certain metals such as lead is well-known. The absorption of even trace amounts of lead can cause severe damage to human organs. The numerous and widespread sources of lead in the environment, including the food supply, compounds the problems of screening affected groups.

It is generally recognized that lead poisoning occurs in children at blood levels as low as 10–15 ug/dl. Lead contamination of environmental sources such as water, dust and soil require identification at even lower levels. To measure these amounts, the analytical techniques must be sensitive, contaminant-specific, and reliable.

The use of d-aminolevulinic acid dehydratase (ALAD) activity in red blood cells to determine exposure to environmental lead is described by A. Berlin, et al., "European Standardized Method for the Determination of d-Aminolevulinic Acid Dehydratase Activity in Blood," *Z. Klin. Chem. Klin. Biochem.*, 12 Jg. 1974, S. 389–390. The assay entails incubation of the enzyme with excess d-aminolevulinic acid (ALA). The porphobilinogen (PBG) which is formed within a predetermined time interval is mixed with modified Ehrlich's reagent, and the color developed is measured photometrically against a blank. The quantity of PBG produced is a measurement of the ALAD activity corresponds to low levels of lead exposure.

The method of colorimetric determination of ALAD was originally disclosed by K. D. Gibson, et al., "The Purification and Properties of d-Aminolaevulic Acid Dehydrase," *Bioch.*, 61:618–629 (1955). In addition to a purification method, this reference discloses the activation of the ALAD by thiol reagents and the inhibition of the dehydrase activity by copper, mercury and silver.

Subsequently, a modified colorimetric method for lead detection was presented by S. Sassa, "Delta-Aminolevulinic Acid Dehydratase Assay," *Enzyme*, 28:133–145 (1982). As part of the assay disclosed, the mercury containing compound $HgCl_2$ is used with trichloroacetic acid (TCA) to precipitate proteins as well as in the modified Ehrlich's reagent to eliminate interference with chromophore formation by sulfhydryl compounds. The reduction effect of sulfhydryl compounds like dithiothreitol (DTT), mercaptoethanol, cysteine and reduced glutathione to increase enzyme activity is also disclosed. The instability of the sulfhydryl compounds require special preparation for their use in the assay.

Two articles, each entitled "Purification and Properties of d-Aminolevulinate Dehydrase from Human Erythrocytes," first published by P. Anderson, et al., *J. Biol. Chem.*, 254:6924–6930 (1979) and subsequently by P. Gibbs, et al., *Biochem J.*, 230:25–34 (1985), disclose assays demonstrating lead as a noncompetitive inhibitor of ALAD activity. The incubation mixtures contained DTT, ALAD and ALA in a buffer solution. The incubations were terminated by the addition of TCA which also contained $HgCl_2$. The solution was centrifuged and the supernatant was added to modified Ehrlich's reagent in acetic acid and perchloric acid. The colored complex formed with PBG was measured spectrophotometrically.

A similar assay measuring the activity of ALAD after exposure to lead containing samples is disclosed in a published PCT application WO 93/01310 to Silbergeld. The application suggests utilizing other well-known methods like conjugating or attaching a label to either the substrate or product and quantifying the amount of labeled material present after a defined reaction period. Another approach suggested, uses a known antibody that binds specifically to unoccupied lead binding sites of ALAD.

A significant problem in using an ALAD assay is the toxicity of the mercury used in the TCA solution as well as in the modified Ehrlich's reagent to eliminate interference with chromophore formation by sulfhydryl compounds. The disposal of mercury-containing waste products also causes an environmental problem which increases the relative expense of using the assay.

Accordingly, there is a need to replace mercury with a reagent which is less toxic and environmentally hazardous without diminishing the sensitivity and accuracy of the assay. The present invention provides selected metal ions used as colorimetric enhancing reagents to replace mercury in the assays.

Another solution to the problem is to eliminate using mercury altogether. One inventive approach is to replace the prior art sulfhydryl compounds with a reagent which can increase an enzyme's activity without requiring a metal ion like mercury for its effective use.

Although phosphines have been disclosed for reducing proteins, their utility has been limited because they are malodorous, insoluble in water, and those with low molecular weights easily autoxidate. For example, tertiary phosphines are disclosed as reductive agents to cleave gamma-globulin in M. E. Levison, et al., "Reduction of Biological Substances by Water-Soluble Phosphines: Gamma-Globulin (IgG)," *Experientia*, 25:126–7 (1969). A tertiary phosphine is disclosed by T. L. Kirley, "Reduction and Fluorescent Labeling of Cyst(e)ine-Containing Proteins for Subsequent Structural Analyses," *Analytical Biochemistry*, 180:231–236 (1989) as part of the process to reduce and alkylate proteins. Furthermore, as disclosed by J. A. Burns, et al., "Selective Reduction of Disulfides by Tris(2-carboxyethyl) phosphine" *J. Org. Chem.*, 56:2648–2650 (1991), qualitative studies of the relative reactivity of the tertiary phosphine with lipoic acid and 2-hydroxyethyl disulfide indicated that the reductions are kinetically, not thermodynamically, controlled.

The present invention provides selected water-soluble tertiary phosphines used as activating reagents to improve the sensitivity and accuracy of a lead assay. The inventive activating reagents replace the prior art sulfhydryl compounds and eliminate using mercury in the assays. In some assays, an inventive activating reagent can be used in combination with an inventive colorimetric enhancing reagent for further improvement of the assay's sensitivity and accuracy.

SUMMARY OF THE INVENTION

The present invention provides a method of improving the sensitivity and accuracy of a lead assay for a sample solution suspected of containing lead. The assay determines the extent of a reaction between a substrate and a disulfide enzyme. The improvement includes reducing the disulfide enzyme with a water-soluble tertiary phosphine reagent so as to increase the activity of the disulfide enzyme for reaction with the substrate. Preferably, tris(2-carboxyethyl)phosphine is used as the water-soluble tertiary phosphine for increasing the activity of the enzyme.

The method of improving the sensitivity and accuracy of a lead assay includes incubating an aminolevulinic acid dehydratase enzyme in a sample solution suspected of containing lead in the presence of a water-soluble tertiary phosphine and a substrate containing aminolevulinic acid to form a product containing porphobilinogen. The enzyme incubation step is stopped after a predetermined time interval and the extent of the incubation reaction is determined.

The present invention also provides an activating reagent for increasing the enzymatic activity of ALAD to improve the sensitivity and accuracy of a lead assay. The activating reagent includes a water-soluble tertiary phosphine.

Another method contemplated by the present invention includes incubating a disulfide enzyme in a sample solution suspected of containing lead in the presence of a reducing reagent and a substrate to form a reaction product. The enzyme incubation step is stopped after a predetermined time interval and a chromophore is formed upon reaction with a selected component of the sample solution in the presence of a colorimetric enhancing reagent. The colorimetric enhancing reagent contains a metal ion soluble in the sample solution which is selected from the group consisting essentially of a cupric ion and a ferric ion. The extent of the chromophore formation is then photometrically determined. A kit for performing the above lead assays is also provided.

Another reagent provided by the present invention is a colorimetric enhancing reagent for improving the sensitivity and accuracy of photometrically determining the activity of a disulfide enzyme in a lead assay. The colorimetric enhancing reagent contains a metal ion soluble in a solution containing the product of the enzyme activity. The metal ion is selected from the group consisting essentially of a cupric ion and a ferric ion.

Accordingly, it is an advantage of the present invention to provide reagents for a more sensitive and accurate lead assay using a disulfide enzyme.

Another advantage of the present invention is to provide reagents which simplify a lead assay by eliminating the need to remove interfering precipitates.

A further advantage of the present invention is to provide a substitute reagent for mercury which is less toxic and environmentally hazardous without diminishing the sensitivity and accuracy of the lead assay.

Yet another advantage of the present invention is to provide reagents which eliminate the use of mercury in colorimetric lead assays.

Other and further advantages, embodiments, variations and the like will be apparent to those skilled in the art from the present specification taken with the appended claims.

DETAILED DESCRIPTION

The present invention relates to simplifying and improving the sensitivity and accuracy of an assay for determining lead by exposing an ALAD enzyme to a sample such as whole blood and measuring the inhibition of activity. Preparation for the assay includes pretreating the sample to expose and recover the lead from within the red blood cells and to precipitate interfering compounds such as proteins, endogenous ALAD, PBG, ALA and the like. Acid such as TCA, nitric acid, 5-sulfosalicylic acid, or perchloric acid is commonly used to pretreat the sample. The interfering compounds are then pelleted by centrifugation leaving a supernatant which contains the lead isolated from the interfering compounds.

The acidified supernatant containing the recovered lead is then separated for additional processing. The supernatant must be neutralized prior to incubation of the ALAD enzyme. A neutralizing reagent is added to bring the supernatant sample to a neutral pH.

An enzyme reagent containing ALAD and a substrate like ALA is added to the neutralized sample. The enzyme reagent also contains a sulfhydryl compound like DTT to increase the enzyme activity of ALAD. The neutralized sample is then incubated to promote the reaction between the ALAD and ALA and produce the product PBG.

After a predetermined time interval, the incubation or reaction between the ALAD and ALA is stopped by adding a stop reagent. The stop reagent commonly contains an acid such as TCA which stops further incubation. The stop reagent also commonly contains mercury compound such as $HgCl_2$ to release the $Hg^{+2}$ metal ion in the sample solution.

Adding the stop reagent to the sample solution produces a precipitate which potentially interferes with the determination of the amount of the product resulting from the assay which in this case is PBG. Accordingly, prior art lead assays usually require performing the two steps of removal and separation of the precipitate before the extent of the enzyme and substrate reaction is determined. Centrifugation is commonly used to remove the precipitate from the sample solution. The resulting supernatant contains the PBG which is then separated from the precipitate for further processing.

A colorimetric determination of the reaction product is widely used. In this technique, Ehrlich's reagent is added to the sample solution after the supernatant is separated from the precipitate to form a chromophore upon reaction with the PBG. Often, the Ehrlich's reagent is modified to contain a mercury compound to provide a $Hg^{+2}$ metal ion in the sample solution which precipitates sulfhydryl compounds interfering with the chromophore formation. The precipitation of the sulfhydryl compounds by the mercuric ion improves the sensitivity and accuracy of the assay.

The present invention has found certain activating reagents which improve the sensitivity and accuracy of a lead assay by increasing the activity of a disulfide enzyme reacting with a substrate. The inventive activating reagents eliminate the use of both the sulfhydryl compounds like DTT and the mercury containing compounds. It is believed that the inventive activating reagents reduce the disulfide bonds of the enzyme to enhance or increase the activity of the enzyme.

The inventive activating reagents also provide a more simple and convenient assay method. Unlike the sulfhydryl compounds, the inventive activating reagents do not interfere with the chromophore reaction of the assay. Furthermore, the inventive activating reagents do not need to be removed from the sample solution by forming a precipitate. Thus, two entire steps of the prior art assay are eliminated. Since the present invention avoids forming a precipitate, there is no need to centrifuge the sample solution and separate the reaction product contained in the supernatant for further processing.

The inventive activating reagents contain a water-soluble tertiary phosphine. A preferred water-soluble tertiary phosphine is tris(2-carboxyethyl)phosphine (TCEP). Other suitable tertiary phosphines include tributylphosphine, tris(4-carboxyphenyl)phosphine and tris(hydroxymethyl)phosphine. The effect of the inventive activating reagents is apparent at very low concentrations. A preferred concentration for using the water-soluble tertiary phosphine is greater than about 0.5 mM in the enzyme reagent. Above this concentration the improvement levels off.

The inventive activating reagents can be used with many different techniques to determine the extent of the incubation reaction between the disulfide enzyme and the substrate. Any component of the sample solution can be directly analyzed after the incubation reaction has been stopped. For example, this includes measuring the amount of the reaction product made or the starting reactants consumed.

Use of the inventive activating reagents also allows indirect determination of the amount of the substrate utilized or the PBG produced. Other reactants can be added to the sample solution for a subsequent reaction therewith. For example, an assay can be performed by competitively binding a suitable antibody to the PBG or to a fluorophore-PBG complex, and measuring the resultant fluorescent polarization level. Another example is a REA assay which adds a subsequent fluorophore and measures the fluorescence quench by the chromophore. In another example, an antibody which binds specifically to the substrate or the to the product can be used in a suitable assay like ELISA, sandwich assay, agglutination assay, RIA and the like. Still another example is to label the substrate with a detectable characteristic and, subsequently, determine the extent the label is affected by the assay.

The present invention has also found certain colorimetric enhancing reagents can be substituted for the mercuric ion in either the stop reagent or Ehrlich's solution or both. These inventive colorimetric enhancing reagents are relatively less toxic and environmentally hazardous than the mercuric ion.

A preferred colorimetric enhancing reagent is the cupric ion $Cu^{+2}$ and any compound which contains the cupric ion is suitable for use in the present invention. The cupric ion provides a significant improvement in the sensitivity and accuracy of the assay as compared to using the mercuric ion. A preferred concentration range for the cupric ion is an amount in excess of 100 mM to about 500 mM. The range of 5 mM to about 100 mM is also suitable.

When used in the assay with one of the above described activating reagents, the inventive cupric ion demonstrates a further dramatic gain in sensitivity and accuracy than by using the activating reagent alone. The currently preferred activating reagent to use in this combination is TCEP.

The inventive colorimetric enhancing reagents can be used with the conventional sulfhydryl compounds like DTT. The present invention eliminates using the mercuric compound while the sensitivity and accuracy of the assay is significantly improved. Furthermore, the inventive colorimetric reagents do not form a precipitate with the sulfhydryl compounds, so the step of removing the precipitate is eliminated.

Another inventive colorimetric enhancing reagent contemplated by the present invention is the ferric ion and any compound which contains the ferric ion is suitable for use by the present invention. The ferric ion provides a comparable sensitivity and accuracy when used in the assay when compared to the mercuric ion. Preferably, the ferric ion is used in combination with a sulfhydryl compound like DTT. A preferred concentration range is about 10 mM to about 100 mM although amounts in excess of this level are also suitable.

As used herein, the term "colorimetric enhancer" means a reagent provided by the present invention that increases the accuracy and sensitivity of a lead assay in comparison to that achieved by the assay in the absence of the reagent. It is believed that the colorimetric enhancer reagent eliminates interference by sulfhydryl compounds with chromophore formation using a coloring reagent.

A coloring reagent is added to the sample solution to form a chromophore upon reaction with the product or other preselected reactant found in the sample solution. Suitable coloring reagents for use in the present invention include dimethylaminobenzaldehyde, dimethylaminocinnamaldehyde, or their derivatives.

The inventive colorimetric enhancing reagents are added to the sample solution prior to photometrically determining the extent of the incubation reaction. The addition can take place while adding the stopping reagent or a coloring reagent or both.

The present invention contemplates a method of improving the sensitivity and accuracy of a lead assay. The pretreatment of the sample can be accomplished with conventional techniques such as by adding acid to the whole blood sample.

The acidified sample must then be neutralized before the assay can continue with incubation of the ALAD enzyme. Subsequently, the assay continues by incubating an ALAD enzyme in the sample solution in the presence of a substrate such as ALA.

The enzyme incubation step is stopped after a predetermined time interval by adding a stopping reagent. The stopping reagent contains an acid such as TCA and can also contain one or both of the inventive colorimetric enhancing reagents.

The product of the enzyme activity is PBG. By coloring the PBG with a coloring reagent like Ehrlich's reagent, one can photometrically determine the extent of the enzyme activity. The coloring reagent can contain one or both of the inventive metal ions. It is believed that the inventive metal ions prevent interference of chromophore formation by sulfhydryl compounds.

The following Examples are set forth for the purposes of illustration and should not be construed as limiting.

EXAMPLE 1

Materials

All the reagents used in the present invention are available commercially. The aminolevulinic acid (ALA) and d-aminolevulinic acid dehydratase (ALAD) were both purchased from Sigma Company of St. Louis, Mo., as cat. nos. A-3785 and A-0644, respectively. The $HgCl_2$, dimethylaminobenzaldehyde (DMAB), dithiothreitol (DTT), and trichloroacetic acid (TCA) are also available from Sigma as cat. nos. M-6529, D-8904, D-0632, and D-6399. The buffer (bis[2-hydroxyethyl]iminotris[hydroxymethyl]methane (BisTris) is available from Aldrich Chemical Company of Milwaukee, Wis., as cat. no. 15,666-3. The glacial acetic acid, 60% perchloric acid and concentrated $HNO_3$ acid were purchased from Fisher as cat. nos. A38-212, A228-1, and A200-212.

The L-histidine monohydrochloride monohydrate (Histidine) and Iminodiacetic Acid (IDA) is available from Aldrich as cat. nos. H1,520-9 and I-120-0, respectively. The 10 mg/dl $Pb^{+2}$ volumetric standard was also purchased from Aldrich as cat. no. 31,903-3. The $ZnCl_2$ was purchased from Mallinckrodt as cat. no. 8780.

The $FeCl_3$ and the $CuCl_2-2H_2O$ were purchased from Aldrich as cat nos. 23,648-9 and 30,748-3. The reducing agent Tris(2-carboxyethyl)phosphine Hydrochloride (TCEP-HCL) was obtained from Pierce as cat. no. 20490.

The spectrophotometer used for absorbance measurements was a LKB Ultraspec II Model 4050.

Method

The solutions prepared were stored at room temperature unless otherwise noted. The pH of 50 ml of HPLC grade distilled water was adjusted to a pH 1.50 by adding an appropriate amount of concentrated $HNO_3$. The pH 1.50 distilled water was then added to 0.0340 g. $ZnCl_2$ for a final solution weight of 12,500 g. The solution was then thoroughly mixed.

A neutralizing solution containing 0.5M IDA, 0.125M Histidine and 1.5M BisTris was prepared by adding 7.5 ml of a 2M Bis-Tris solution to following amounts of IDA 0.975 g and Histidine 1.050 g. After stirring, HPLC grade distilled water was added to each neutralizing solution to obtain a final volume of about 9.5 ml. A solution of 200 ml 2M BisTris was prepared by adding 83.60 g of BisTris to HPLC grade distilled water to a final volume of about 180 ml. After stirring, the pH was adjusted to 7.11 with concentrated $HNO_3$. The resulting volume was adjusted to 200 ml with distilled water. The BisTris solution was stirred for 10 min. at room temperature and filtered to remove any visible particles.

A diluted enzyme reagent was prepared by adding 5 ml of ALAD containing 3.1 U/mg to 35 ml of 250 mM BisTris. The 250 mM BisTris diluent solution was prepared by adding 5.23 g. BisTris to 100 ml of HPLC grade distilled water and stirring. DTT was added to 15 mM in the diluted enzyme reagent. The pH of the diluent solution was adjusted to pH 7.0 by adding 50% NaOH. The diluted enzyme reagent was stored at 2°–8° C. under nitrogen gas.

A 25 mM ALA and 10 uM $ZnCl_2$ substrate solution was prepared by adding 0.0127 g. ALA, 30 ul 1 mM $ZnCl_2$ and 3 ml HPLC distilled water to a flask. After stirring, the substrate solution was stored at 2.8° C. in the dark.

A stop reagent containing 10% TCA was prepared by adding 20.000 g of TCA, 0.1M $HgCl_2$ and HPLC grade distilled water to 200 ml. The solution was stirred and filtered at 0.80 um. The various concentrations reported in Table 1 below were prepared by serial dilutions.

For comparison, two inventive stop reagents were prepared by respectively substituting 27 mg of $FeCl_3$ and 26.8 mg of $CuCl_2$ for the $HgCl_2$. The various concentrations reported in Table 1 below were prepared by serial dilutions.

A modified Ehrlich's Reagent was prepared by adding 12.5 g DMAB, 250 ml glacial acetic acid and 122.5 ml of 60% perchloric acid and mixing. The final volume was adjusted to 500 ml by adding more glacial acetic acid. The modified Ehrlich's Reagent was stored in the dark at 2°–8° C.

A 40 ug/dl $Pb^{+2}$ water sample was prepared by dilution of the 0.1 mg/ml lead standard from Aldrich. This dilution was performed with a standard HPLC water that had been pH adjusted to 1.9 with $HN_3$. The pH 1.9 water served as the 0 ug/dl sample. These water samples were neutralized with the neutralizing buffer to pH 7.0. The ratio of the water samples to neutralizing buffer was 60/40.

The assay was run by adding 100 ul of the neutralized water samples to individual polystyrene tubes. The enzyme reagent was added in 100 ul amounts and incubated for 5 minutes at 37° C.

Subsequently 100 ul of the substrate solution was added, mixed by vortexing and incubated for 25 min. in the water bath. The stop reagent was added in an amount of 200 ul and mixed by vortexing. The mixture was centrifuged for two minutes to remove insoluble DTT.

The supernatant mixture was removed and added to 500 ul of the modified Ehrlich's reagent. After incubating for 5 min. at room temperature, the absorbance of the supernatant was recorded at 555 nm.

Results

The absorbance data for each metal ion, $Hg^{+2}$, $Cu^{+2}$, and $Fe^{+3}$, was collected at various concentrations measured in mM. Table 1 shows the measured absorbance at 555 nm. averaged over several trials for each metal ion in the samples containing 0 ug/dl $Pb^{+2}$.

Although all three metal ions gave an increased signal intensity, the effect leveled off before a concentration of about 100 mM was reached for the $Hg^{+2}$ and $Fe^{+3}$ metal ions. The $Cu^{+2}$ metal ion, however, continued to increase the signal intensity beyond the 100 mM concentration level. Accordingly, the procedure was continued at higher concentrations as reported in Table 1.

TABLE 1

| Conc. mM | Average Absorbance at 555 nm | | |
|---|---|---|---|
| | $Cu^{+2}$ | $Fe^{+3}$ | $Hg^{+2}$ |
| 1.0 | 0.696 | 0.650 | 0.500 |
| 5.0 | 1.309 | 0.717 | 1.143 |
| 10.0 | 1.783 | 0.800 | 1.845 |
| 20.0 | 1.782 | 1.177 | 1.840 |
| 50.0 | 1.854 | 1.797 | 1.826 |
| 100.0 | 1.977 | 1.823 | 1.808 |
| 200 | 2.059 | | |
| 300 | 2.192 | | |
| 400 | 2.281 | | |
| 500 | 2.297 | | |

Other metals, including ferrous chloride $FeCl_2$, were tested according to the procedure set forth above. The ferrous chloride, which contains the $Fe^{+2}$ ion, reported an absorbance of only 0.534 at a concentration of 100 mM which was not significantly different than results with no added metal.

EXAMPLE 2

Method

In this example, the same procedure described in Example 1 was used to compare the metal ions using a water soluble tertiary phosphine, TCEP, as a substitute for the reducing agent DTT. The diluted enzyme reagent was prepared as previously described except that TCEP was added to 5 mM in the diluted enzyme reagent instead of the DTT.

Results

The absorbance data for each metal ion, $Hg^{+2}$, $Cu^{+2}$, and $Fe^{+3}$, was collected at various concentrations measured in mM using TCEP rather than DTT in the enzyme reagent. Table 2 shows the measured absorbance span difference for each metal ion between the samples containing 0 ug/dl and 40 ug/dl $Pb^{+2}$. To determine if the effect of $Cu^{+2}$ on signal intensity observed in Example 1 would also be demonstrated using TCEP, the procedure was continued at higher concentrations for the metal ions $Cu^{+2}$ and $Fe^{+3}$ is reported in Table 2. Table 2 also shows an increased absorbance span with $Cu^{+2}$ over $Hg^{+2}$ and $Fe^{+3}$.

TABLE 2

| | Absorbance Span with TCEP | | |
|---|---|---|---|
| Conc. mM | $Cu^{+2}$ | $Fe^{+3}$ | $Hg^{+2}$ |
| 10.0 | 0.978 | 1.053 | 0.915 |
| 20.0 | 0.874 | 1.070 | 0.915 |
| 50.0 | 0.978 | 1.034 | 0.994 |
| 100.0 | 1.066 | 1.091 | 1.020 |
| 200 | 1.250 | 1.125 | |
| 500 | 1.480 | 1.149 | |

EXAMPLE 3

Method

In this example, the same procedure described in Example 1 was used to prepare an enzyme reagent with DTT and a stop reagent with and without $CuCl_2$. As in Example 2, a diluted enzyme reagent was prepared using TCEP added to 5 mM. The same stop reagents with and without $CuCl_2$ were used to compare the effect of DTT and TCEP on the sensitivity of the assay.

Results

The absorbance data for the metal ion $Cu^{+2}$ was collected at concentrations of zero and 400 mM comparing the use of TCEP and DTT in the enzyme reagent. Table 3 shows the measured absorbance span for both concentrations of the metal ion between the samples containing 0 ug/dl and 40 ug/dl $Pb^{+2}$. The use of TCEP provides a significant enhancement of the signal intensity even when the metal ion is eliminated.

TABLE 3

| | Absorbance Span | |
|---|---|---|
| $CuCl_2$ Conc. mM | DTT | TCEP |
| None | 0.476 | 1.045 |
| 400 | 1.490 | 1.458 |

As a matter of convenience, the reagents can be provided as kits, where the reagents are in predetermined ratios, so as to substantially optimize the sensitivity of assay in the range of interest. Wet or dry reagents may be used. After reconstitution of dry reagents, in predetermined volumes, the concentration of the reagents will be at appropriate levels.

The reagents may be mixed with various ancillary materials such neutralizing solutions, buffers, substrate solutions, and the like. The method of the present invention is performed by combining the activating reagent with the ALAD enzyme and the substrate at the time of incubation. The activating reagent may be kept separate or added to either the enzyme solution or the sample containing the ALAD enzyme.

The colorimetric enhancing reagent can be added to the sample at the time the stopping reagent is added or can be added to the sample at the time the coloring reagent is added or both. The colorimetric enhancing reagent may be kept separate or added to either the stopping reagent or to the coloring reagent prior to their addition to the sample.

As demonstrated above, the present invention provides an activating reagent to improve the sensitivity and accuracy of a lead assay using the ALAD enzyme by increasing the activity of the enzyme. The activating reagents were also more stable than the sulfhydryl compounds in the prior art which made the assay easier to use. Also provided are colorimetric enhancing reagents which enhance colorimetric determination without precipitating sulfhydryl compounds.

Use of the activating reagents of the present invention is not limited to photometric analysis of the PBG to determine the lead contamination. The method and reagents of the present invention can be employed in various heterogeneous and homogeneous immunoassay system formats known in the art. Such immunoassay system formats include, but are not intended to be limited to, competitive, sandwich and immunometric techniques. Generally, such immunoassay systems depend upon the ability of a binding member, such as, for example, an immunoglobulin (i.e., a whole antibody or fragment thereof) to bind to a specific analyte from a test sample, wherein a labeled reagent comprising a binding member labeled with a signal generating compound such as a fluorescent or chemiluminescent molecule is employed to determine the extent of binding. Typically, the extent of binding in such immunoassay system formats is determined by the amount of the signal generating compound present in the labeled reagent which either has or has not participated in a binding reaction with the analyte, wherein the signal which is generated by the signal generating compound as described herein is detected and correlated to the amount of analyte present in the test sample. Accordingly, the amount of analyte is correlated to the level of lead contamination of the test sample.

Homogeneous immunoassays typically are performed in a competitive immunoassay format involving a competition between an analyte from a test sample and a labeled reagent for a limited number of receptor binding sites on an antibody to the analyte. The labeled reagent comprises the analyte or analyte-analog labeled with a signal generating compound wherein the concentration of analyte in the test sample determines the amount of the labeled reagent that will specifically bind to the antibody. The amount of the labeled reagent-antibody conjugate produced by such binding may be quantitatively measured and is inversely proportional to the amount of analyte present in the test sample.

Heterogeneous immunoassay formats involve a labeled reagent or tracer comprising an analyte, analyte-analog, or an antibody thereto, labeled with a signal generating compound, to form a free species and a bound species. In order to correlate the amount of tracer in one of such species to the amount of analyte present in the test sample, the free species must first be separated from the bound species, which can be accomplished according to methods known in the art employing solid phase materials for the direct immobilization of one of the binding participants in the binding reaction, such as the antibody, analyte-analog, or analyte, wherein one of the binding participants is immobilized on a solid phase material, such as a test tube, beads, particles, microparticles or the matrix of fibrous material, and the like, according to methods known in the art. The solid phase materials can be any solid material to which a binding participant can be immobilized and include, but are not intended to be limited to, beads, magnetic particles, paramagnetic particles, microparticles or macro particles, test tubes, and microtiter plates. Such solid phase materials can be made from synthetic materials, naturally occurring materials, or naturally occurring materials which have been synthetically modified, and include, but are not intended to be limited to, cellulose materials, such as paper, cellulose and cellulose derivatives such as cellulose acetate and nitrocellulose; fiberglass; naturally occurring cloth such as cotton; synthetic cloth such as nylon; porous gels, such as silica, agarose, dextran, and gelatin; porous fibrous matrixes; starch based materials, such as cross-linked dextran chains; ceramic materials; olefin or thermoplastic materials including polyvinyl chloride, polyethylene, polyvinyl acetate, polyamide, polycarbonate, polystyrene, copolymers of vinyl acetate and vinyl chloride, combinations of polyvinyl chloride-silica; and the like.

Heterogeneous immunoassays can be performed in a competitive immunoassay format wherein, for example, the antibody can be immobilized to a solid phase material whereby upon separation, the signal generated by the signal generating compound of the bound or free species can be detected and correlated to the amount of analyte present in the test sample. Another form of a heterogeneous immunoassay employing a solid phase material is referred to as a sandwich immunoassay, which involves contacting a test sample containing, for example, an antigen with a protein such as an antibody or another substance capable of binding the antigen, and which is immobilized on a solid phase material. The solid phase material typically is treated with a second antigen or antibody which has been labeled with a signal generating compound. The second antigen or antibody then becomes bound to the corresponding antigen or antibody on the solid phase material and the signal generated by the signal generating compound in the bound or the free species can be detected and correlated to the amount of analyte present in the test sample.

The present invention is also not limited to the analysis of lead contamination in a blood sample. The test sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid or the like. The test sample can be pretreated prior to use, such as preparing plasma from blood, diluting viscous fluids, or the like; methods of treatment can involve filtration, distillation, concentration, inactivation of interfering components, and the addition of reagents. Besides physiological fluids, other liquid samples can be used such as water, food products and the like for the performance of environmental or food production assays. In addition, a solid material suspected of containing the analyte can be used as the test sample. In some instances it may be beneficial to modify a solid test sample to form a liquid medium or to release the lead. Generally, any sample suspected of containing lead can be analyzed as long as the lead is liberated from the physical or chemical mixture in which it is presented to produce elemental lead.

While particular embodiments and applications of the present invention have been illustrated and described, it is to be understood that the invention is not limited to the precise construction and compositions disclosed herein and that various modifications, changes, and variations which will be apparent to those skilled in the art may be made in the arrangement, operation, and details of construction of the invention disclosed herein without departing from the spirit and scope of the invention as defined in the appended claims.

What is claimed is:

1. A method for detecting lead in a sample suspected of containing lead, the method comprising:
   (a) forming an aqueous solution from the sample such that any lead in the sample is present in said aqueous solution;
   (b) contacting the aqueous solution with an aminolevulinic acid dehydratase enzyme in the presence of a water soluble tertiary phosphine;
   (c) incubating the enzyme with aminolevulinic acid to form a product comprising porphobilinogen;
   (d) stopping said enzyme incubation performed in step (c) after a predetermined time interval;
   (e) detecting said porphobilinogen resulting from step (c); and
   (f) correlating said porphobilinogen detected in step (e) with the presence of lead in the sample whereas porphobilinogen detected indicates the presence of lead in said sample.

2. The method of claim 1 wherein the water soluble tertiary phosphine reagent is tris(2-carboxyethyl) phosphine.

3. The method of claim 1 wherein the water soluble tertiary phosphine is selected from the group consisting of tributylphosphine, tris(carboxyphenyl)phosphine, and tris(hydroxymethyl)phosphine.

4. The method of claim 1 wherein the method further comprises forming a chromophore with said porphobilinogen in the presence of a colorimetric enhancing reagent, said colorimetric enhancing reagent comprising a cupric ion soluble in the aqueous solution.

5. The method of claim 4 wherein the colorimetric enhancing reagent is added directly to the aqueous solution after incubation of the aminolevulinic acid dehydratase and aminolevulinic acid in step (c).

6. The method of claim 1 wherein the method comprises acidifying the aqueous solution to isolate the lead from compounds which interfere with said method, said compounds being selected from the group consisting of proteins, endogenous d-aminolevulinic acid dehydratase, porphobilinogen and aminolevulinic acid, and neutralizing the aqueous solution before said enzyme incubation of step (c).

7. The method of claim 1 wherein the stopping step includes acidifying the aqueous solution and adding a coloring reagent to form a chromophore upon reaction with said porphobilinogen.

8. The method of claim 7 wherein the coloring reagent is selected from the group consisting of dimethylaminobenzaldehyde and dimethylaminocinnamaldehyde.

9. The method of claim 1 wherein the stopping step includes forming a chromophore upon reaction of a coloring reagent with the porphobilinogen in the presence of a colorimetric enhancing reagent, the colorimetric enhancing reagent comprising a cupric ion soluble in the aqueous solution; and wherein step (e) includes photometrically detecting said chromophore.

10. The method of claim 9 wherein the cupric ion is present in an amount of about 1 mM to about 500 mM.

11. A method for detecting lead in a sample suspected of containing lead, the method comprising:
   (a) forming an aqueous solution from the sample such that any lead in the sample is present in said aqueous solution;

(b) incubating in said aqueous solution, (i) an aminolevulinic acid dehydratase enzyme; and (ii) aminolevulinic acid, in the presence of a reducing agent, to form porphobilinogen;

(c) stopping said enzyme incubation of step (b) after a predetermined time interval;

(d) contacting the porphobilinogen formed in step (b) with a coloring reagent to form a chromophore, in the presence of a metal ion selected from the group consisting of cupric ion and ferric ion;

(e) photometrically detecting said chromophore resulting from step (d); and (f) correlating the chromophore detected in step (e) with the presence of lead in the sample whereas the presence of the chromophore detects lead in the sample.

12. The method of claim 11 wherein the method further includes acidifying the aqueous solution to isolate the lead in the solution from compounds which interfere with said method, said compounds being selected from the group consisting of proteins, endogenous d-aminolevulinic acid dehydratase, porphobilinogen and aminolevulinic acid, and neutralizing the aqueous solution before said enzyme incubation of step (b).

13. The method of claim 11 wherein step (c) includes acidifying the aqueous solution and adding a coloring reagent to the solution.

14. The method of claim 13 wherein the coloring reagent is selected from the group consisting of dimethylaminobenzaldehyde and dimethylaminocinnamaldehyde.

15. The method of claim 11 wherein said metal ion is cupric ion present in an amount of about 100 mM to about 500 mM.

16. The method of claim 11 wherein said metal ion is ferric ion present in an amount of about 10 mM to 100 mM.

17. The method of claim 11 wherein the reducing agent comprises dithiothreitol.

18. A lead assay reagent composition comprising (i) an aminolevulinic acid dehydratase enzyme, or its substrate aminolevulinic acid; and (ii) a water soluble tertiary phosphine.

19. The reagent composition of claim 18 wherein the water soluble tertiary phosphine is selected from the group consisting of tris(2-carboxyethyl)phosphine tributylphosphine, tris(carboxyphenyl)phosphine, and tris(hydroxymethyl)phosphine.

20. The reagent composition of claim 18 wherein the reagent composition further comprises a colorimetric enhancing reagent, said colorimetric enhancing reagent comprising a cupric ion soluble in the reagent composition.

21. The reagent composition of claim 20 wherein the cupric ion is present in an amount of about 100 mM to about 500 mM.

22. A lead assay reagent composition comprising (i) a metal ion selected from the group consisting of cupric ion and ferric ion, and (ii) a coloring reagent capable of forming a photometrically detectable chromophore upon reaction with porphobilinogen.

23. The reagent composition of claim 22 wherein the coloring reagent is selected from the group consisting of dimethalaminobenzaldehyde and dimethalaminocinnemaldehyde.

24. The reagent composition of claim 22 wherein the reagent composition further comprises a trichloroacetic acid stop reagent for stopping the reaction between said enzyme and said aminolevulinic acid.

25. The reagent composition of claim 22 wherein the reagent is cupric ion present in an amount of about 100 mM to about 500 mM.

26. The reagent composition of claim 22 wherein the reagent is ferric ion present in an amount of about 10 mM to 100 mM.

27. A kit for performing an assay for lead on a sample suspected of containing lead, the kit comprising (i) a first container comprising an aminolevulinic acid dehydratase enzyme; (ii) a second container, separate from said first container, comprising aminolevulinic acid, wherein said first or said second container further comprises a water soluble tertiary phosphine.

28. The kit of claim 27 wherein the kit further includes a container comprising (i) a stop reagent which stops the reaction between the aminolevulinic acid and aminolevulinic acid dehydratase enzyme and (ii) a coloring reagent which forms a chromophore upon reaction with porphobilinogen.

29. The kit of claim 28 wherein the stop reagent further comprises a colorimetric enhancing reagent, said colorimetric enhancing reagent containing a cupric ion soluble in the stop reagent.

30. The kit of claim 27 wherein said water soluble tertiary phosphine is tris(2-carboxyethyl) phosphine.

31. The kit of claim 27 wherein the water soluble tertiary phosphine is selected from the group consisting of tributylphosphine, tris(carboxyphenyl)phosphine, and tris(hydroxymethyl)phosphine.

32. A kit for performing an assay on a sample suspected of containing lead, the kit comprising:

a container comprising a substrate aminolevulinic acid;

a container comprising an aminolevulinic acid dehydratase enzyme;

a container comprising a trichloroacetic acid stop reagent effective for stopping the reaction between the substrate and the enzyme, a coloring reagent for forming a chromophore upon reaction with porphobilinogen, and a colorimetric enhancing reagent for improving the sensitivity and accuracy of photometrically determining the extent of the chromophore formation, said colorimetric enhancing reagent comprising a metal ion soluble in the stop reagent selected from the group consisting of cupric ion and ferric ion; and a reducing reagent present in either the substrate container, or the enzyme container in an amount effective to increase reaction of the enzyme with said substrate.

33. The kit of claim 32 wherein the colorimetric enhancing reagent is cupric ion present in an amount of about 100 mM to about 500 mM.

34. The kit of claim 32 wherein the colorimetric enhancing reagent is ferric ion present in an amount of about 10 mM to 100 mM.

35. The kit of claim 32 wherein the reducing agent comprises dithiothreitol.

36. The kit of claim 32 wherein the coloring reagent is selected from the group consisting of dimethylaminobenzaldehyde and dimethylaminocinnamaldehyde.

* * * * *

UNITED STATES PATENT AND TRADEMARK OFFICE
CERTIFICATE OF CORRECTION

PATENT NO. : 5,552,297
DATED : September 3, 1996
INVENTOR(S) : Wong, et Al.

It is certified that error appears in the above-indentified patent and that said Letters Patent is hereby corrected as shown below:

Column 8, line 1, change "HN$_3$" to --HNO$_3$--.

Signed and Sealed this

Eighteenth Day of February, 1997

Attest:

BRUCE LEHMAN

Attesting Officer     Commissioner of Patents and Trademarks